(12) United States Patent
McGuan et al.

(10) Patent No.: US 8,794,977 B2
(45) Date of Patent: Aug. 5, 2014

(54) IMPLANT TRAINING SYSTEM

(75) Inventors: Shawn Patrick McGuan, San Clemente, CA (US); Jonathan Kirk Nielsen, Dana Point, CA (US); Ted Schwartz, San Clemente, CA (US)

(73) Assignee: LifeModeler, Inc., San Clemente, CA (US)

( * ) Notice: Subject to any disclaimer, the term of this patent is extended or adjusted under 35 U.S.C. 154(b) by 445 days.

(21) Appl. No.: 12/770,532

(22) Filed: Apr. 29, 2010

(65) Prior Publication Data

US 2010/0332194 A1    Dec. 30, 2010

Related U.S. Application Data

(60) Provisional application No. 61/173,886, filed on Apr. 29, 2009.

(51) Int. Cl.
*G09B 23/28* (2006.01)
*A61F 2/38* (2006.01)

(52) U.S. Cl.
USPC ...... 434/262; 434/274; 623/20.14; 623/20.15

(58) Field of Classification Search
USPC ............. 434/262; 600/300; 604/890.1, 891.1; 623/11.1, 13.12
See application file for complete search history.

(56) References Cited

U.S. PATENT DOCUMENTS

| | | |
|---|---|---|
| 4,528,980 A | 7/1985 | Kenna |
| 5,234,433 A | 8/1993 | Bert et al. |
| 5,299,893 A | 4/1994 | Salyer et al. |
| 5,425,368 A | 6/1995 | Brandt |
| 5,682,886 A | 11/1997 | Delp et al. |
| 5,709,689 A | 1/1998 | Ferrante et al. |
| 5,798,924 A | 8/1998 | Eufinger et al. |
| 5,951,605 A | 9/1999 | Dennis et al. |
| 6,205,411 B1 * | 3/2001 | DiGioia et al. ................. 703/11 |
| 6,327,491 B1 | 12/2001 | Franklin et al. |
| 6,423,077 B2 | 7/2002 | Carol et al. |
| 6,529,762 B1 | 3/2003 | Ladebeck |
| 7,427,200 B2 * | 9/2008 | Noble et al. .................. 434/274 |
| 7,618,451 B2 | 11/2009 | Berez et al. |

(Continued)

FOREIGN PATENT DOCUMENTS

| | | |
|---|---|---|
| WO | WO9400056 A1 | 1/1994 |
| WO | WO9625114 A1 | 8/1996 |

(Continued)

OTHER PUBLICATIONS

International Search Report and Written Opinion for International Application No. PCT/US2011/040042, mailed Feb. 17, 2012.

(Continued)

*Primary Examiner* — Robert J Utama
*Assistant Examiner* — Sadaruz Zaman
(74) *Attorney, Agent, or Firm* — Fish & Richardson P.C.

(57) ABSTRACT

An implant training system based on a biomechanical modeling system is disclosed. In one embodiment, the implant training system includes a processor configured to load and execute instructions from an implant simulation module and the implant simulation module configured to provide a preloaded case representing a model patient to a user, receive input from the user to adjust the preloaded case to represent a particular patient, and provide outcome information for using an implant in the particular patient.

24 Claims, 11 Drawing Sheets

(56) References Cited

U.S. PATENT DOCUMENTS

| | | | |
|---|---|---|---|
| 8,425,524 | B2 | 4/2013 | Aker et al. |
| 2001/0001120 | A1 | 5/2001 | Masini |
| 2002/0055783 | A1 | 5/2002 | Tallarida et al. |
| 2002/0115934 | A1* | 8/2002 | Tuke ............................ 600/473 |
| 2002/0180760 | A1 | 12/2002 | Rubbert et al. |
| 2003/0000535 | A1 | 1/2003 | Galloway et al. |
| 2003/0045885 | A1 | 3/2003 | Margulies et al. |
| 2003/0060890 | A1 | 3/2003 | Tarabishy |
| 2003/0078587 | A1 | 4/2003 | Lechot et al. |
| 2004/0030245 | A1* | 2/2004 | Noble et al. ................. 600/426 |
| 2004/0153079 | A1 | 8/2004 | Tsougarakis et al. |
| 2004/0260301 | A1 | 12/2004 | Lionberger et al. |
| 2005/0075649 | A1 | 4/2005 | Bova et al. |
| 2005/0148843 | A1 | 7/2005 | Roose |
| 2006/0161051 | A1* | 7/2006 | Terrill-Grisoni et al. ..... 600/300 |
| 2006/0276786 | A1 | 12/2006 | Brinker |
| 2007/0106299 | A1 | 5/2007 | Manspeizer |
| 2007/0123912 | A1 | 5/2007 | Carson |
| 2007/0198022 | A1 | 8/2007 | Lang et al. |
| 2007/0219639 | A1 | 9/2007 | Otto et al. |
| 2007/0270680 | A1 | 11/2007 | Sheffer et al. |
| 2007/0276224 | A1 | 11/2007 | Lang et al. |
| 2008/0009952 | A1 | 1/2008 | Hodge |
| 2008/0154269 | A1 | 6/2008 | Roger |
| 2008/0171932 | A1 | 7/2008 | Yan et al. |
| 2008/0188855 | A1 | 8/2008 | Brown |
| 2008/0242953 | A1* | 10/2008 | Dew et al. .................... 600/300 |
| 2008/0312663 | A1 | 12/2008 | Haimerl et al. |
| 2008/0319448 | A1 | 12/2008 | Lavallee et al. |
| 2008/0319491 | A1 | 12/2008 | Schoenefeld |
| 2009/0088753 | A1 | 4/2009 | Aram et al. |
| 2009/0088755 | A1 | 4/2009 | Aker et al. |
| 2009/0088763 | A1 | 4/2009 | Aram et al. |
| 2009/0093816 | A1 | 4/2009 | Roose |
| 2009/0138020 | A1 | 5/2009 | Park et al. |
| 2009/0163922 | A1 | 6/2009 | Meridew et al. |
| 2009/0171184 | A1 | 7/2009 | Jenkins et al. |
| 2009/0227905 | A1 | 9/2009 | Warkentine et al. |
| 2009/0281415 | A1 | 11/2009 | Cupps et al. |
| 2009/0318976 | A1 | 12/2009 | Gabriel et al. |
| 2010/0023015 | A1 | 1/2010 | Park |
| 2010/0030231 | A1 | 2/2010 | Revie et al. |
| 2010/0076563 | A1* | 3/2010 | Otto et al. .................. 623/20.14 |

FOREIGN PATENT DOCUMENTS

| | | | |
|---|---|---|---|
| WO | WO2004078078 | A1 | 9/2004 |
| WO | WO2006078236 | A1 | 7/2006 |
| WO | WO2009075562 | A1 | 6/2009 |
| WO | WO2009106816 | A1 | 9/2009 |

OTHER PUBLICATIONS

Visionaire Patient Matched Instrumentation—A technology from Smith & Nephew Design Rationale, 7 pages (2008).
Office Action for U.S. Appl. No. 12/746,272, mailed Jun. 18, 2013.
International Search Report for International Application No. PCT/US2012/040373, mailed Oct. 23, 2012.
International Search Report for International Application No. PCT/US2011/047897, mailed Mar. 27, 2012.
International Search Report for International Application No. PCT/US2011/047860, mailed Mar. 19, 2012.
International Search Report for International Application No. PCT/US2011/047936, mailed Mar. 26, 2012.
International Search Report for International Application No. PCT/US201/047671, mailed Mar. 28, 2012.
International Search Report for International Application No. PCT/US2011/047675, mailed Feb. 29, 2012.
International Search Report for International Application No. PCT/US2011/047674, mailed Mar. 5, 2012.
International Preliminary Report on Patentability for International Application No. PCT/US2011/047674, mailed Feb. 19, 2013.
International Search Report for International Application No. PCT/US2011/047670, mailed Mar. 19, 2012.
International Preliminary Report on Patentability for International Application No. PCT/US2011/047670, mailed Feb. 19, 2013.
International Search Report for International Application No. PCT/US2011/056380, mailed May 21, 2012.
International Preliminary Report on Patentability for International Application No. PCT/US2011/056380, mailed Apr. 16, 2013.
International Search Report for International Application No. PCT/US2011/085897, mailed May 28, 2009.
International Preliminary Report on Patentability for International Application No. PCT/US2011/085897, mailed Jun. 8, 2010.
International Preliminary Report on Patentability for International Application No. PCT/US2011/040042, mailed Dec. 27, 2012.
International Search Report and Written Opinion for International Application No. PCT/US2011/040031, mailed Feb. 17, 2012.
International Preliminary Report on Patentability for International Application No. PCT/US2011/040031, mailed Dec. 27, 2012.
Office Action for U.S. Appl. No. 13/157,991, mailed Jan. 15, 2014.

* cited by examiner

IMPLANT TRAINING SYSTEM

RELATED APPLICATION

The present application claims priority to U.S. provisional patent application Ser. No. 61/173,886 filed Apr. 29, 2009, entitled "Knee Arthroplasty Training Tool Using a Surgical Procedure Viewer-Based Extraction Methodology to Draw From a Computational Modeling Database of Predicted Outcomes", which is incorporated herein by reference in its entirety.

BACKGROUND

1. Field of Invention

The present invention relates to biomechanical modeling, more particularly the invention relates to biomechanical modeling for surgeons operating or preparing for surgery.

2. Related Art

Software based biomechanical modeling has been used extensively in product development departments for many major orthopedic companies for several years. This software empowers the engineer with a detailed understanding of joint kinematics, contact forces, and tissue forces for knee arthroplasty, and other joint replacements. This knowledge has been used successfully to advance the design of knee implants and other implants and replacements including hips, shoulders and the spine.

A significant effort is involved by these orthopedics companies to convey this detailed understanding of knee function to the consumer (the surgeon). This is currently done using diagrams, videos and presentations. This very high cost effort and involves many highly skilled staff.

In addition, with the surge in even more complicated and higher functioning knee implant systems, surgeon education effort is even more vital, stressing the resources of the orthopedics companies. The higher functioning knee implants typically require a modification to the surgical skill set of the surgeon.

Thus, a system and method to address this educational gap by providing a simple, easy-to-use computer based tool to draw on the knowledge base of the knee product design engineers is desired.

SUMMARY

The present invention provides a software tool or system to be used by orthopedic surgeons performing surgery related to biomechanics (e.g., knee arthroplasty). The system may include a database of variations of arthroplasty with their predicted or potential outcomes. For other applications, a database of variations of treatments and their predicted outcomes may be used. The system also provides a display which provides access to the database of potential outcomes by interacting with it via a surgical protocol-based format.

In one embodiment, the implant training system includes a processor configured to load and execute instructions from an implant simulation module and the implant simulation module configured to provide a preloaded case representing a model patient to a user, receive input from the user to adjust the preloaded case to represent a particular patient, and provide outcome information for using an implant in the particular patient. While the description below is focused on the modeling system for use in the knee, the modeling system may be used for any surgery related to biomechanics.

BRIEF DESCRIPTION OF THE DRAWINGS

These and other aspects, advantages and details of the present invention, both as to its structure and operation, may be gleaned in part by a study of the accompanying exemplary drawings, in which like reference numerals refer to like parts. The drawings are not necessarily to scale, emphasis instead being placed upon illustrating the principles of the invention.

DETAILED DESCRIPTION

Certain embodiments as disclosed herein provide for methods and systems for allowing a user (e.g., surgeon) to interact with implants via a software tool, such as simulating surgery using a specific implant. After reading this description it will become apparent how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

As is known, each implant (e.g., implant type) has a unique geometry intended by its designers to solve specific sets of problems. Differences in geometry can drastically affect the mechanical environment of a joint—the way it moves, the mechanical advantage of different muscles, and forces placed on surrounding tissues, such as ligaments. For example, one implant might be designed to feel more "stable" to the patient by filling more of the void left by removed bone. As a result, it might be less forgiving to malalignment, because it is inherently closer to a "too tight" condition in which it stretches surrounding soft tissues.

In another example, an implant might have a prominent ridge, lip, or other feature that could rub and irritate soft tissues if not aligned correctly, whereas the surgeon might be accustomed to a smooth, rounded implant that is forgiving to different alignments. Consequently, the implant type and specific implant configuration often require the surgeon to modify his surgical skill set in order to properly select and successfully place the implant in a patient.

Figure 1:
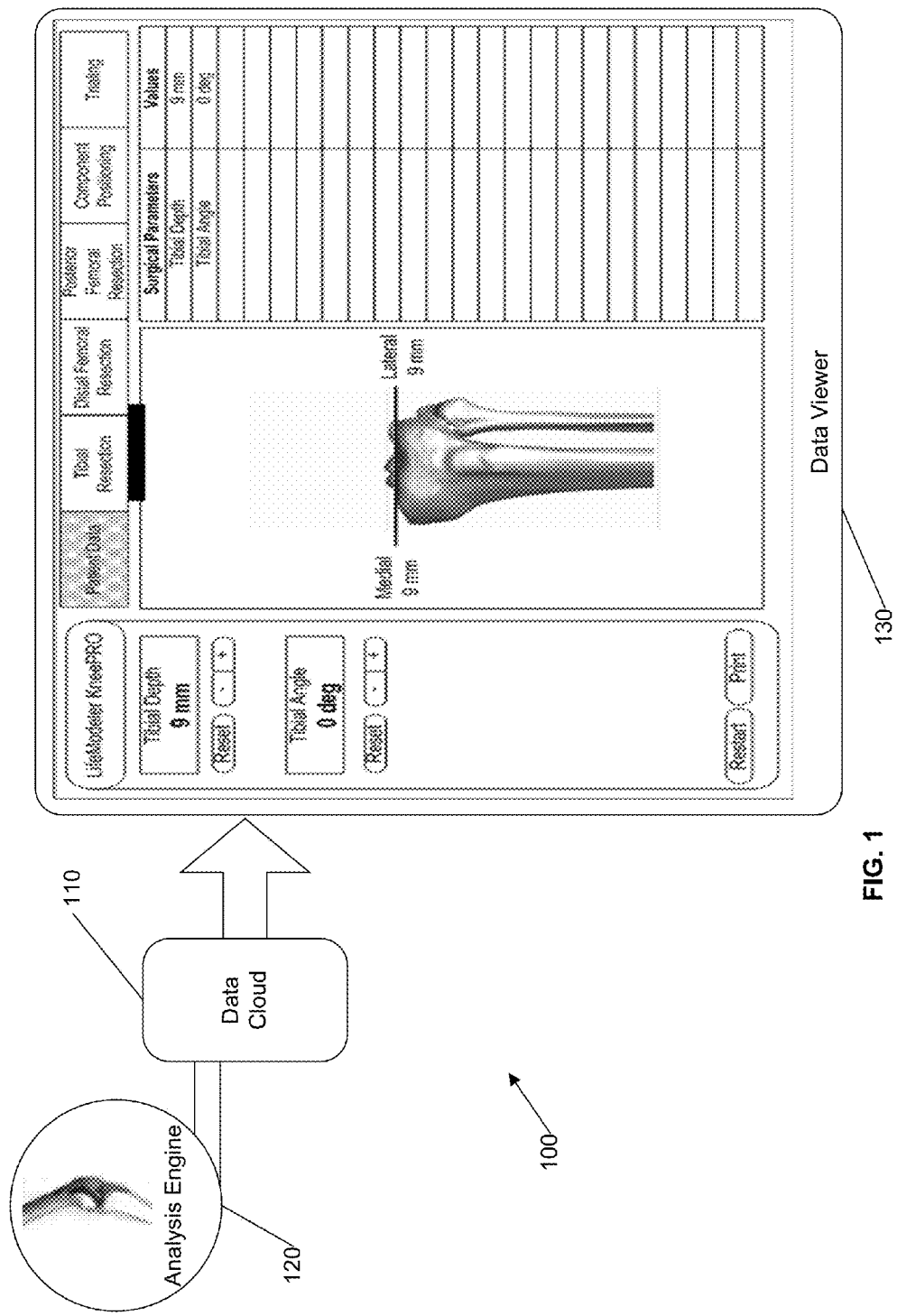
FIG. 1 is a block diagram of data flow in accordance with an embodiment of the invention.

Turning to FIG. 1, data flow for a system 100 in accordance with an embodiment is shown. System 100 includes a database or data cloud 110 of surgical outcomes for various surgical implantation and component alignment techniques. For example the data can be generated using software based biomechanical modeling (e.g, using analysis engine 120) that has been used extensively in product development department for many major orthopedic companies for several years. For example, analysis engine 120 may include a computer simulation tool, such as LifeMOD/KneeSIM, previously run for a range of test cases expected to include a case of interest. Generally, data cloud 110 uses the input parameters to incorporate the results from analysis engine 120 for a case with similar inputs, for example, interpolating between similar cases.

As used herein, a database includes succinct data information. In contrast, a data cloud includes succinct data information as well as tools to manipulate the data (e.g., algorithms) to derive secondary information (e.g., such as by interpolation). Both of these types of data storage (database or data cloud) may be referred to generally as a datastore.

Alternatively, database or data cloud 110 data may come from a large set of clinical data, such as subject outcomes. Alternatively, database or data cloud 110 data may come from a simulation of the case of interest being performed on request.

Database or data cloud 110 can contain some or all possible combinations of surgical alignment for various implant systems (surgical technique or parameters) of interest and individual patient considerations. The data cloud 110 may be populated for a specific patient, using patient data such as a digital X-ray, CT scan or a MRI scan. Alternatively, the data cloud 110 can be populated based upon the data of an example subject or by the data from small or large numbers of individuals.

The surgeon would then use a display 130 generated by the viewer of the system 100 to set up the surgical technique or enter the desired surgical parameters. As used herein, the viewer or viewer system includes the implant simulation module as well as the hardware needed to implement the implant simulation module. The data associated with the selected technique would then be used to extract the associated outcome in the data cloud 110.

It should be appreciated that the analysis engine 120 and/or data base or data cloud 110 may be located on the same computer system as the viewer system. Alternatively, the engine 120 and/or data base or data cloud 110 may be located on a different computer system from the viewer system. As an example, the viewer system may be implemented by the computer system shown in FIG. 11.

As is known, implant designers offer a range of implant sizes based on data from historical sales data, intra-operative atomic measurements, and medical imaging studies (e.g., MRI and CT). The implant shapes are designed to function with typical anatomy. Exceptions are custom-made implants, which are uncommon and expensive. Variations in patient anatomy and implant alignment are sometimes studied by designers to avoid product designs that are particularly sensitive to these factors. This can be done through computer simulation or physical testing, but is not universally performed.

Final decision for implant and size selection, position, and alignment are left to the surgeon. These decisions are typically made based on training and experience with similar patients and implants. New implants, therefore, usually require a period of experimentation, during which the surgeon develops the experience to make informed decisions about implanting the new device.

While the example described in conjunction with FIG. 1, describes using LifeMOD/KneeSIM for the analysis engine 120, other analysis tools may be used. Currently, LifeMOD/KneeSIM is a widely-used simulation tool for knee replacement. LifeMOD tools can also be used for other joints. Similar tools using multi-body dynamics solvers haven been developed by various researchers (e.g., University of Kansas, Southampton University, etc.) but are not commercially available at this time.

Some dedicated biomechanics modeling programs with custom solver engines are available commercially, including SIMM, AnyBody and OpenSIM. These tools may include the ability to calculate three dimensional contact between bodies, which may be a requirement to accurately model complex joints like the knee. Additionally, finite element analysis (FEM) is common among biomechanics researchers, and may be used to generate results necessary to populate database 110.

Figure 2:
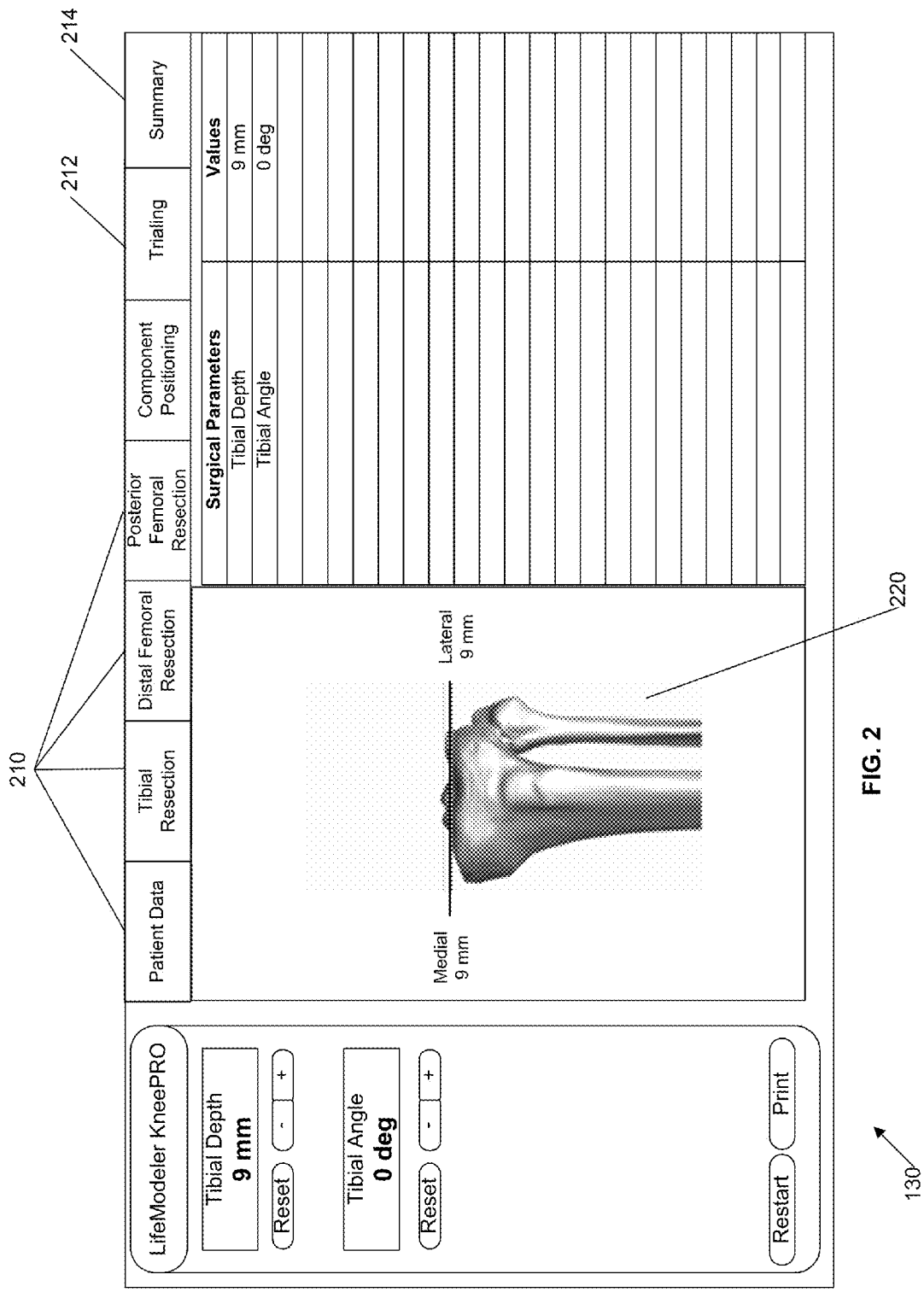
FIG. 2 is an exemplary screen shot of a display of a viewer system in accordance with an embodiment of the invention.

Turning now to FIG. 2, a more detailed view of display 130 generated by the viewer system is shown. The tabs 210 at the top of screen 130 represent specific surgical steps in the knee arthroplasty procedure. For example, in any surgery procedure, tissue resection (e.g., tibial and femoral as shown in tabs 210) and component or implant positioning is adjusted by the user (e.g., surgeon) by entering patient information in the display 130. The bones of the patient (a specific patient or an example subject) are displayed by the system in the window 220.

The surgeon interacts with the viewer system by specifying details of the specific surgical approach for the patient (e.g., cut location and angle) via the display 130. The surgical approach may be provided by the implant or device manufacturer, as a surgical technique document is generally distributed with each product. The surgical technique document usually includes an outline of the surgical procedure to implant the device, and is usually written with input from surgeons who were involved in the development and testing of the device.

Although the steps to perform a particular procedure, such as total knee replacement, are broadly the same for any product, the specific surgical technique is unique to each product due to differences in instrumentation or implant design. The order of steps may be changed for specific implant systems to reflect a particular alignment or tissue management philosophy, or specific alignment tools or cutting grades may accompany the implant. Generally, the implant manufacturers are responsible for publishing the surgical technique document at the introduction of a new product and updating it if needed as new experience with the device becomes available.

As used herein, the surgical technique describes the steps needed to complete a procedure on a normal, uncomplicated case. The surgeon must make adjustments to deal with different patient factors. These subtleties of technique are sometimes problematic because surgeons experienced with a procedure often forget that a new device may require adjustments in technique.

In the example depicted in FIG. 2, the tibial resection parameters (depth and angle) are being selected. In embodiments directed to other replacements, corresponding bones and resections and implant position would be addressed. The other categories of parameters to be selected by the surgeon for the procedure are represented by some of the other tabs 210 of the viewer system and interactions with those sections of the display of the viewer system operate in a similar manner.

The system allows the surgeon to adjust the "cuts" by interacting with the controls on the left panel with the display changing to indicate the currently entered choices. Other methods for inputting the surgeon's choices can also be used.

In one embodiment, the trialing tab 212 of the viewer system displays the consequences of the surgical decisions made up to this point. For example, selecting the trialing tab 212 after some or all of the applicable decisions (e.g., depth and angle in the example shown in FIG. 2) for the surgery have been selected causes the system to extract the outcome from the database and present the results to the surgeon in a simple good/bad format for various parameters.

In one embodiment the good/bad determination is made based on a mathematical expression using the data from each analysis. This expression can be specific to a particular implant or surgeon, based on manufacturer recommendations or experience. The surgeon then can pursue more details of the results (e.g., the data from the data cloud 110 associated with the outcome), hence, increasing the knowledge of the consequences of his surgical decisions. For example, the results of analyses replicating the clinical tests a surgeon might perform can be shown. For example, for knee arthroplasty, rocking the tibia medially and laterally relative to the femur, and evaluating the gaps that open up at each side of the knee may be shown.

In some embodiments, because quantitative results are available in the outcome database, for a particular measure (e.g., ligament tension), a numeric value may be displayed. To more quickly communicate the information to the user, however, the output may be simplified to a visual indicator, such as a red or green color, depending on whether the calculated output value fell within or outside a predefined range of acceptable values. The acceptable range may be defined by experienced surgeons familiar with the device, or according to individual surgeon preference.

The summary tab 214 of the viewer system displays information regarding the pre-op and post-op patient parameters (e.g., mechanical alignment or deformity), as well as a record of all the surgical parameters. Generally, the surgical parameters are captured from user inputs to system 100. These parameters are intended to represent the decisions that are made intra-operatively by the surgeon (e.g., how much bone thickness to resect and at what angle). This information, along with patient parameters and outcome measures, provide a complete record of the procedure that could be available for later study/review.

This surgical information could be used to build an understanding of the effects of various decisions when reviewing outcomes. In addition, more detailed information regarding the kinematic and kinetic performance of the implant during functional activities such as walking, sitting, and squatting may also be displayed here.

An exemplary scenario guiding a surgeon using the system 100 will now be described. Unless specified otherwise, FIGS. 3-10 illustrate actions performed by the viewer system. Also, references to anatomy (e.g., body tissues) and implants are intended to be references to representations in the system 100 (e.g. underlying data).

Example

Figure 3:
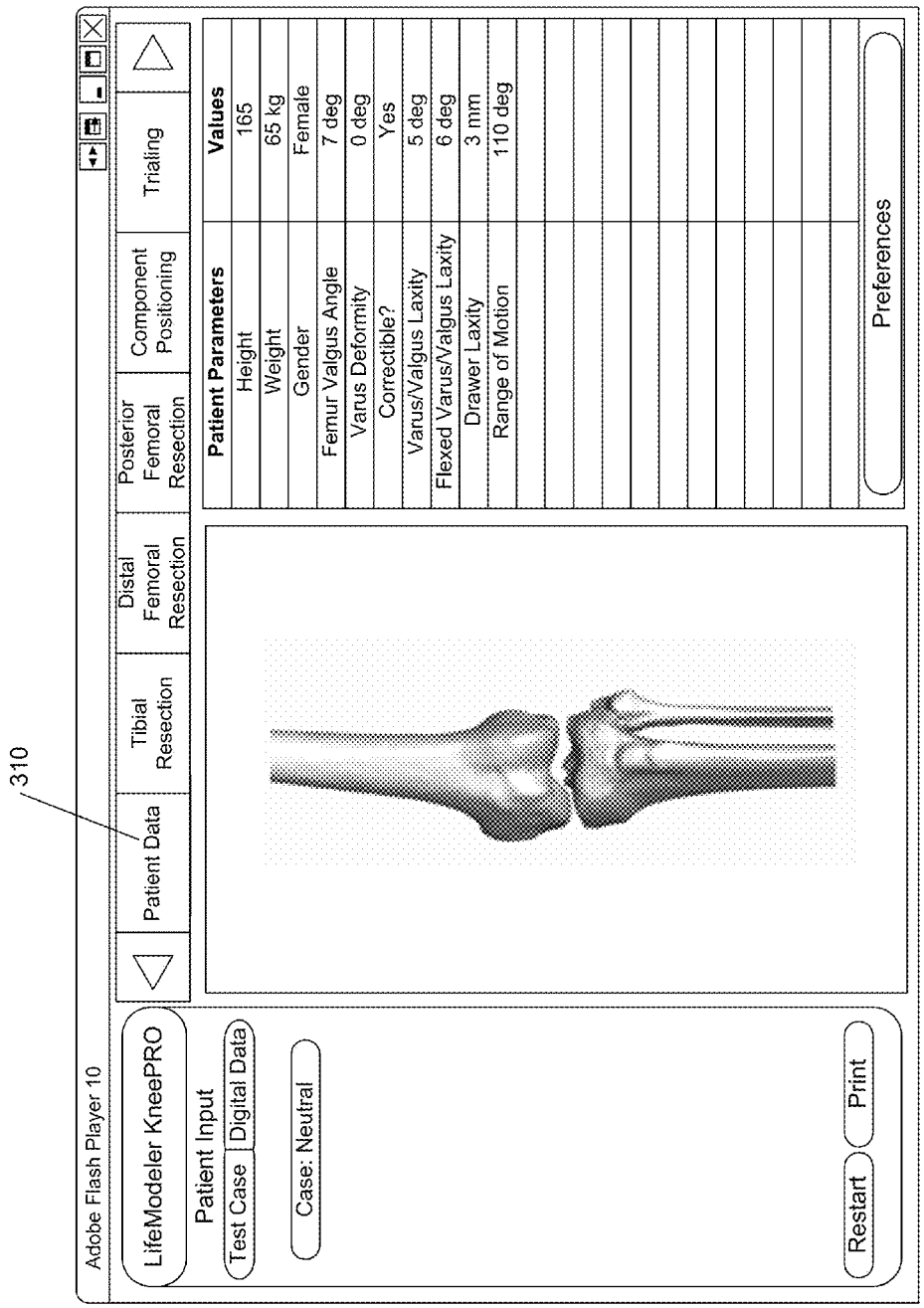
FIG. 3 is an exemplary screen shot of a display of a viewer system in accordance with an embodiment of the invention.

Turning now to FIG. 3, in a first step, the user launches the software application for joint modeling (also referred to interchangeably as implant training application described in further detail in FIG. 11). In some embodiments, the joint modeling application of the viewer system produces the display 130 of the viewer system of FIG. 2. Thus, the joint modeling application receives data from database 110, which may be produced by analysis engine 120. The joint modeling application may be launched from a desktop icon, and run locally from the user's computer, tablet, smart phone, or other electronic device. Alternatively, the joint modeling application may be accessed via the internet, and run on a remote server.

Upon launching the joint modeling application, a display or screen 300 displays a preloaded case representing a model patient. Alternatively, data on a specific patient could be loaded at this point. This specific patient data may be entered by the user by selecting (e.g., clicking on entry fields) pre-designated or predetermined parameters and filling in the data. Additional patient data, for example X-ray, CT scan or an MRI scan, may be extracted from the data cloud 110. The patient data (presented on patient data tab 310), regardless of source (e.g., a simulated subject or a particular patient, etc.) is the starting point for the rest of the simulation. This patient data, combined with the desired surgical parameters, determines the outputs displayed. Patient data includes factors that can be measured on the patient prior to surgery: height, weight, disease state, etc.

Figure 4:
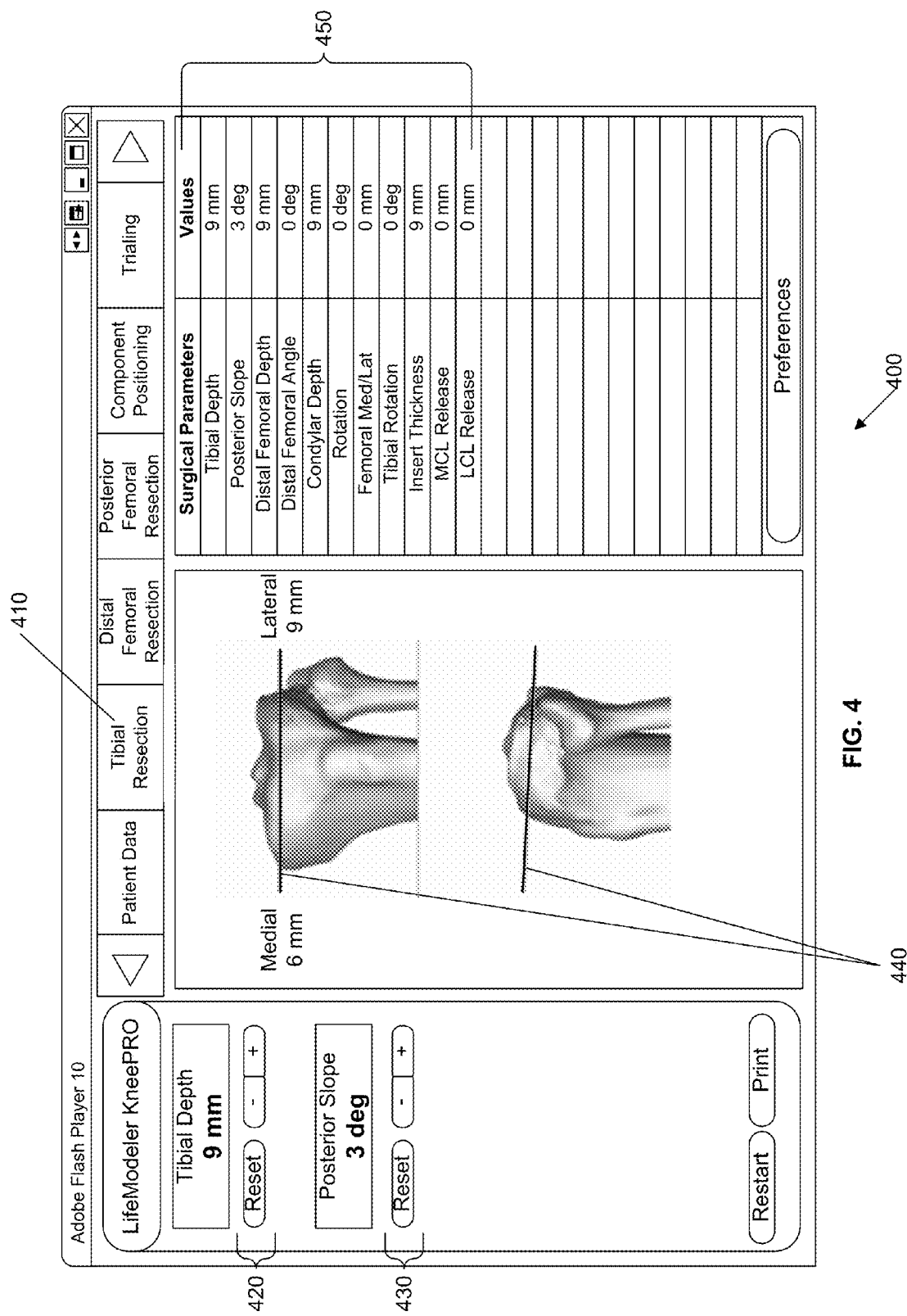
FIG. 4 is an exemplary screen shot of a display of a viewer system in accordance with an embodiment of the invention.

Referring now to FIG. 4, the user may next select the tibial resection tab 410 of the viewer system, as shown on screen 400. On tibial resection tab 410, the user can adjust both the depth and the angle of the resection on the tibia. Lines 440 on the bones indicate where the cut will be made with the current settings, and clicking on control buttons 410 and 420 moves the resection lines to indicate different cut positions. For example, control buttons 420 allow the user to increase (+), decrease (−), or reset the tibial depth; control buttons 430 allow the user to increase (+), decrease (−), or reset the posterior slope. The options selected on this step are captured in the surgical parameters list 450. This list of parameters is updated at each step (e.g., tab), and the values are used at the end of the procedure to calculate results.

The options available on tibial resection tab 410 reflect the decisions that a surgeon makes while performing this part of a knee replacement surgery. If a tibial resection is not necessary, this tab 410 may not be used by the surgeon.

Figure 5:
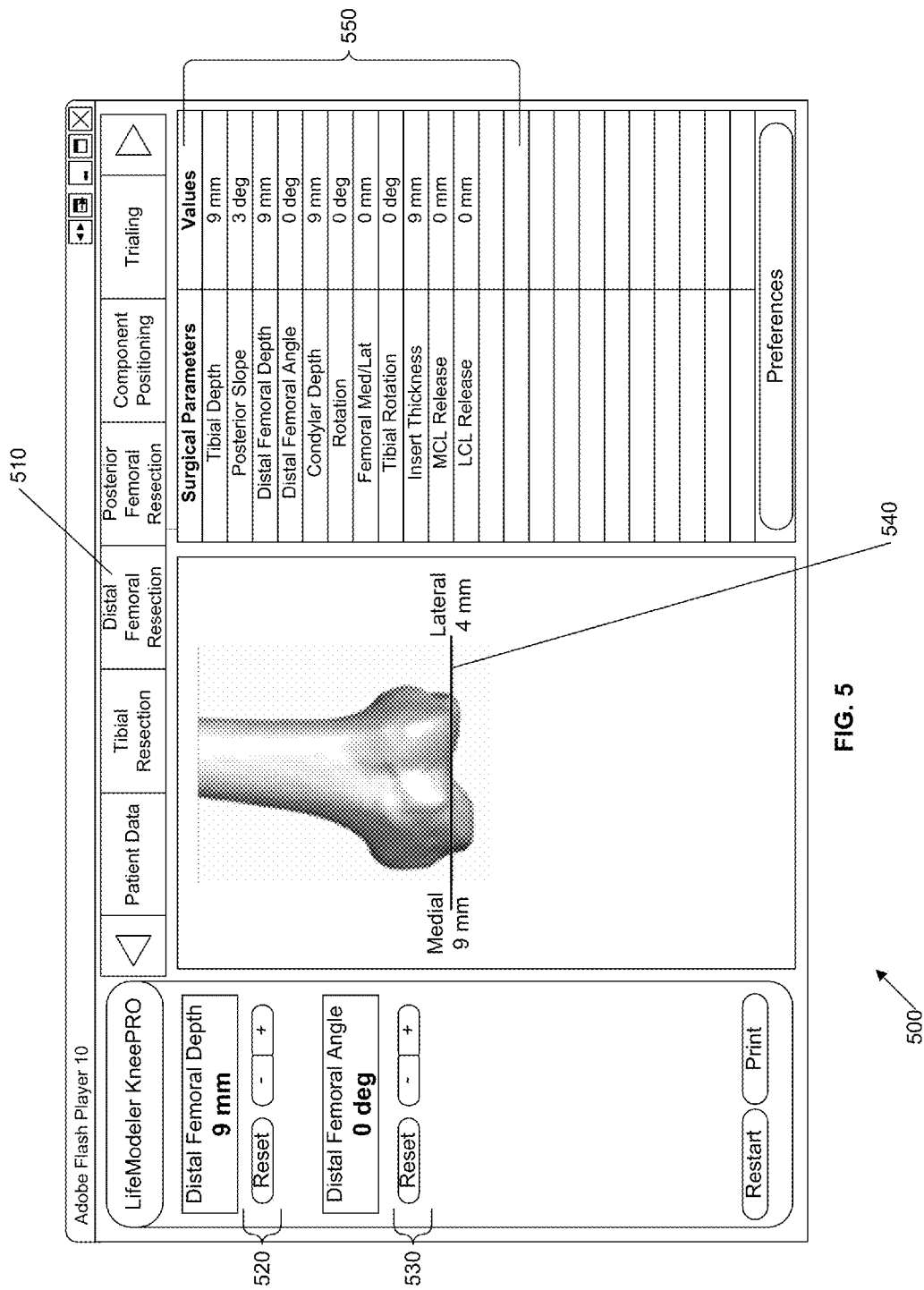
FIG. 5 is an exemplary screen shot of a display of a viewer system in accordance with an embodiment of the invention.

Referring now to FIG. 5, the user may select the distal femoral resection tab 510 of the viewer system, as shown on screen 500. On the distal resection tab 510, the user adjusts the controls 520 and 530 to manipulate the distal resection on the femur. For example, control buttons 520 allow the user to increase (+), decrease (−), or reset the distal femoral depth; control buttons 530 allow the user to increase (+), decrease (−), or reset the distal femoral angle. Once again, the line 540 on the bone image indicates the location of the resection.

The decisions made by the user with regard to the distal resection are captured in the surgical parameters list or table 550. Both the depth (thickness) and angle of the distal resection can be varied in this step, according to the standard surgical procedure or other known information. Once again, if a distal femoral resection is not necessary, this tab 510 may not be used by the surgeon.

Figure 6:
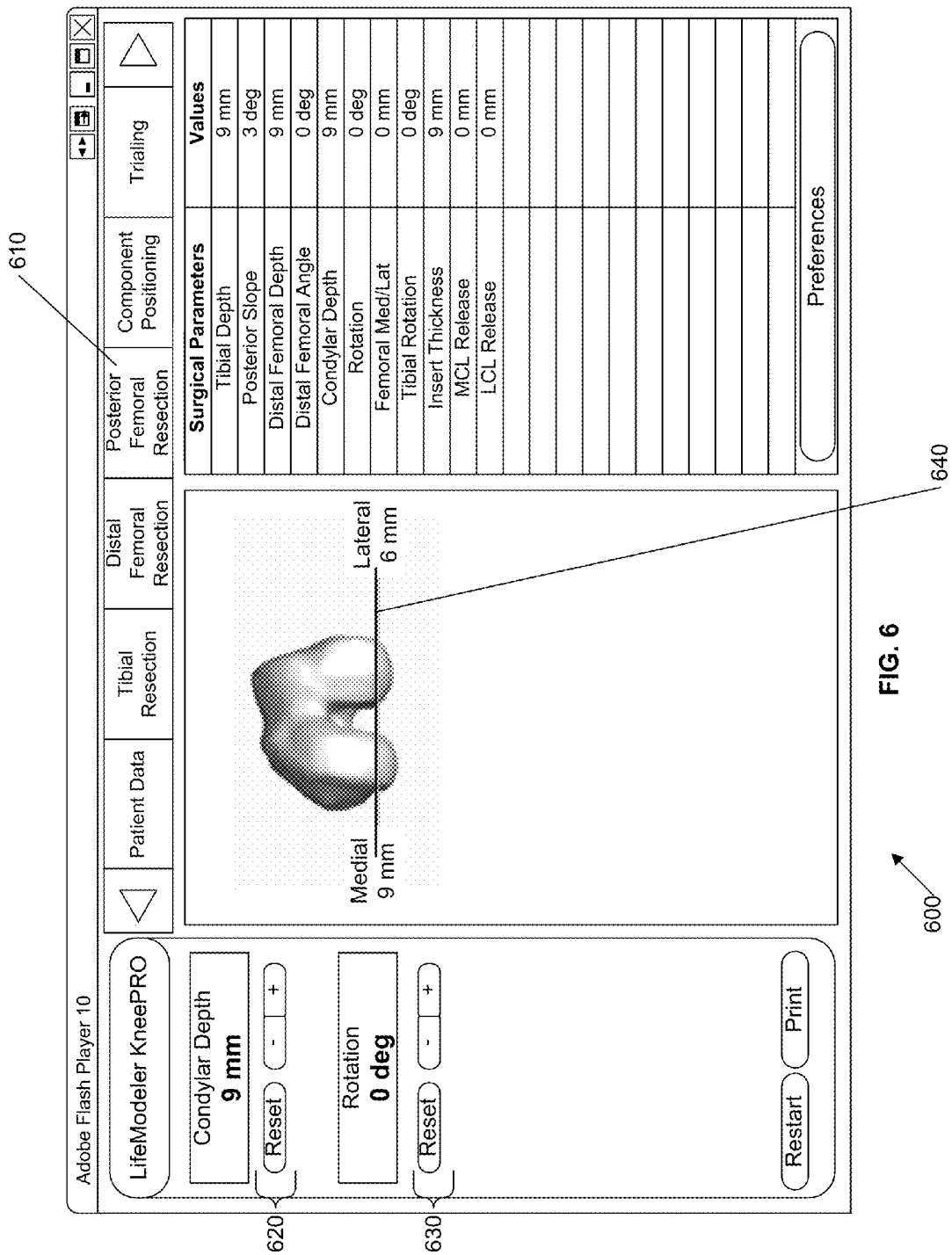
FIG. 6 is an exemplary screen shot of a display of a viewer system in accordance with an embodiment of the invention.

Referring now to FIG. 6, the user may select the posterior femoral resection tab 610 of the viewer system, as shown on screen 600. On tab 610, the user sets the depth and angle of the posterior cut on the distal femur. This is done by adjusting controls 620 and 630 to manipulate the posterior resection on the femur. For example, control buttons 620 allow the user to increase (+), decrease (−), or reset the condylar depth; control buttons 630 allow the user to increase (+), decrease (−), or reset the rotation. As in the other resection tabs, the line 640 indicates the position of the resection on the bone image. The thickness of material removed on the medial and lateral aspects of the bone is displayed on the image, and is updated with changes to the resection location.

Figure 7:
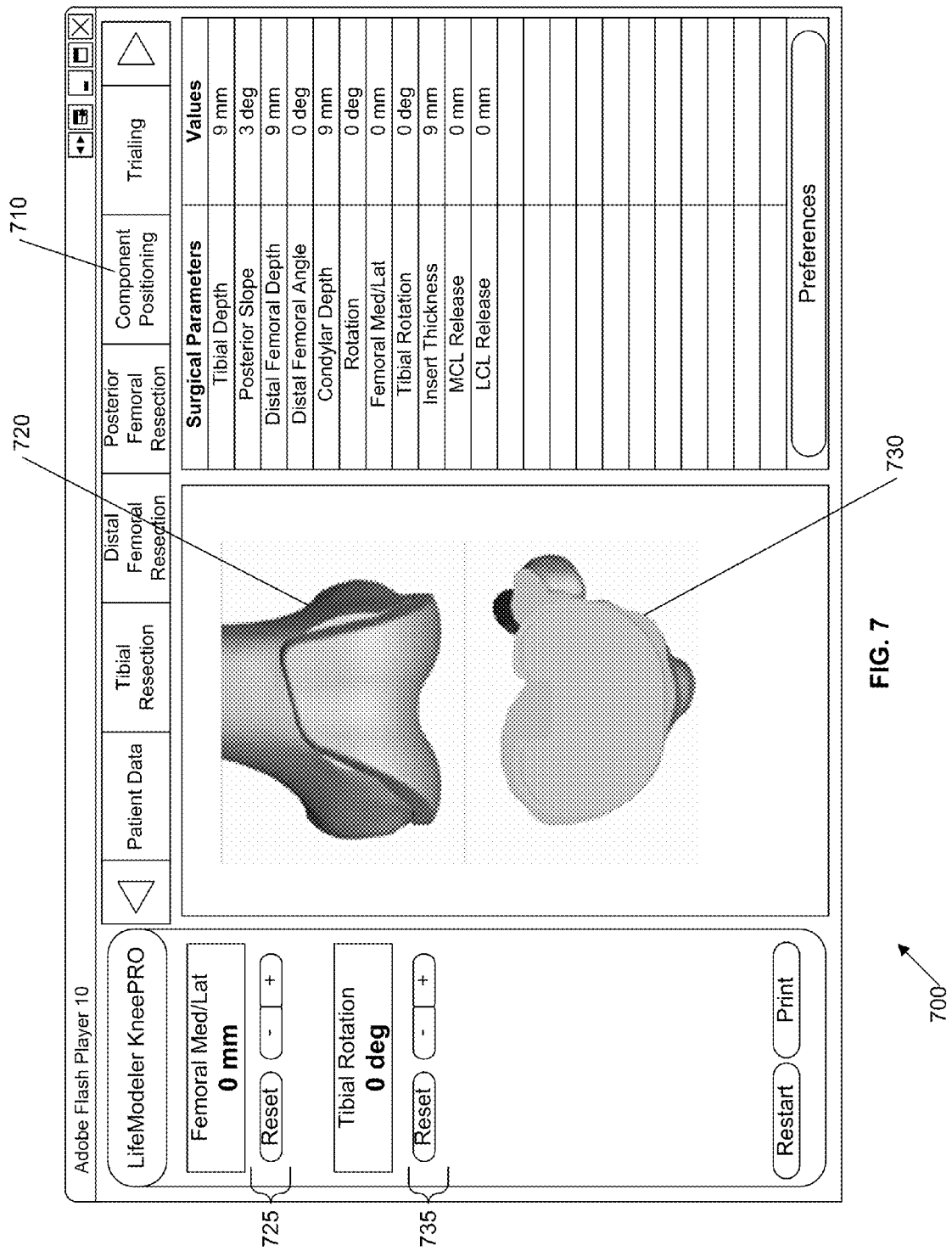
FIG. 7 is an exemplary screen shot of a display of a viewer system in accordance with an embodiment of the invention.

Referring now to FIG. 7, the user may select the component positioning tab 710 of the viewer system, as shown on screen 700. On the component positioning tab 710, the user has the opportunity to adjust the positions and alignment of the femoral implant or component 720 and tibial implant or component 730 on the cut bone surfaces. The image of FIG. 7 has the resected bone with the implant, properly placed, shown on top of the bone. The position of the implant relative to the bone moves based on the adjustment parameters. For example, the femoral component 720 can be moved side to side in the medial/lateral direction by control buttons 725, and the tibial component 730 can be rotated on the cut surface of the bone by control buttons 735.

Generally, the goal for the surgeon in this step is to align the implants so they cover the resected bone surface as completely as possible, and so the components are mechanically aligned with the anatomy, especially soft tissues, which affect the transmission of forces through the implants. The images of the components 720, 730 move relative to the bones to indicate the positioning and alignment scenario selected using the control buttons 725, 735.

Figure 8:
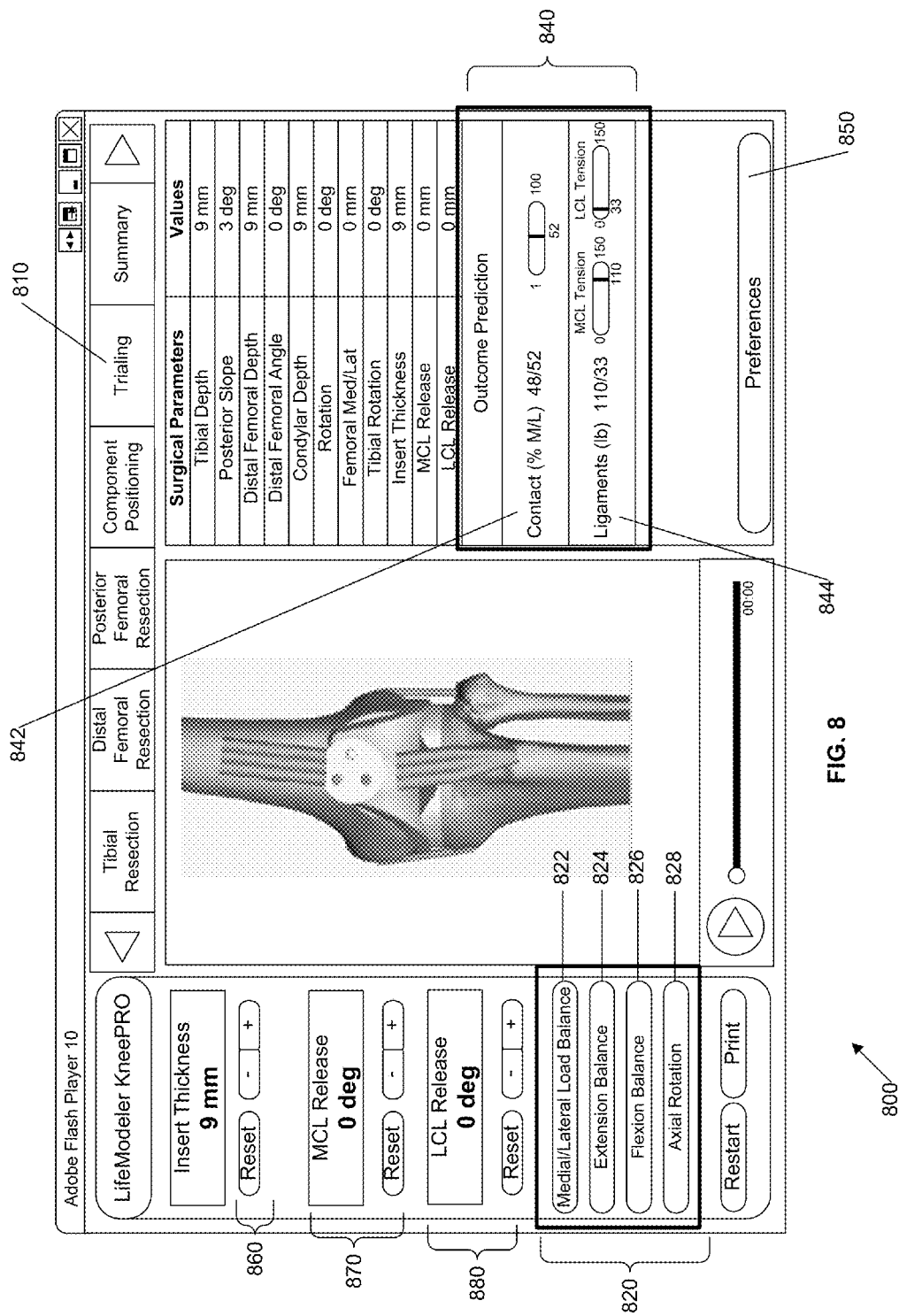
FIG. 8 is an exemplary screen shot of a display of a viewer system in accordance with an embodiment of the invention.
Figure 9:
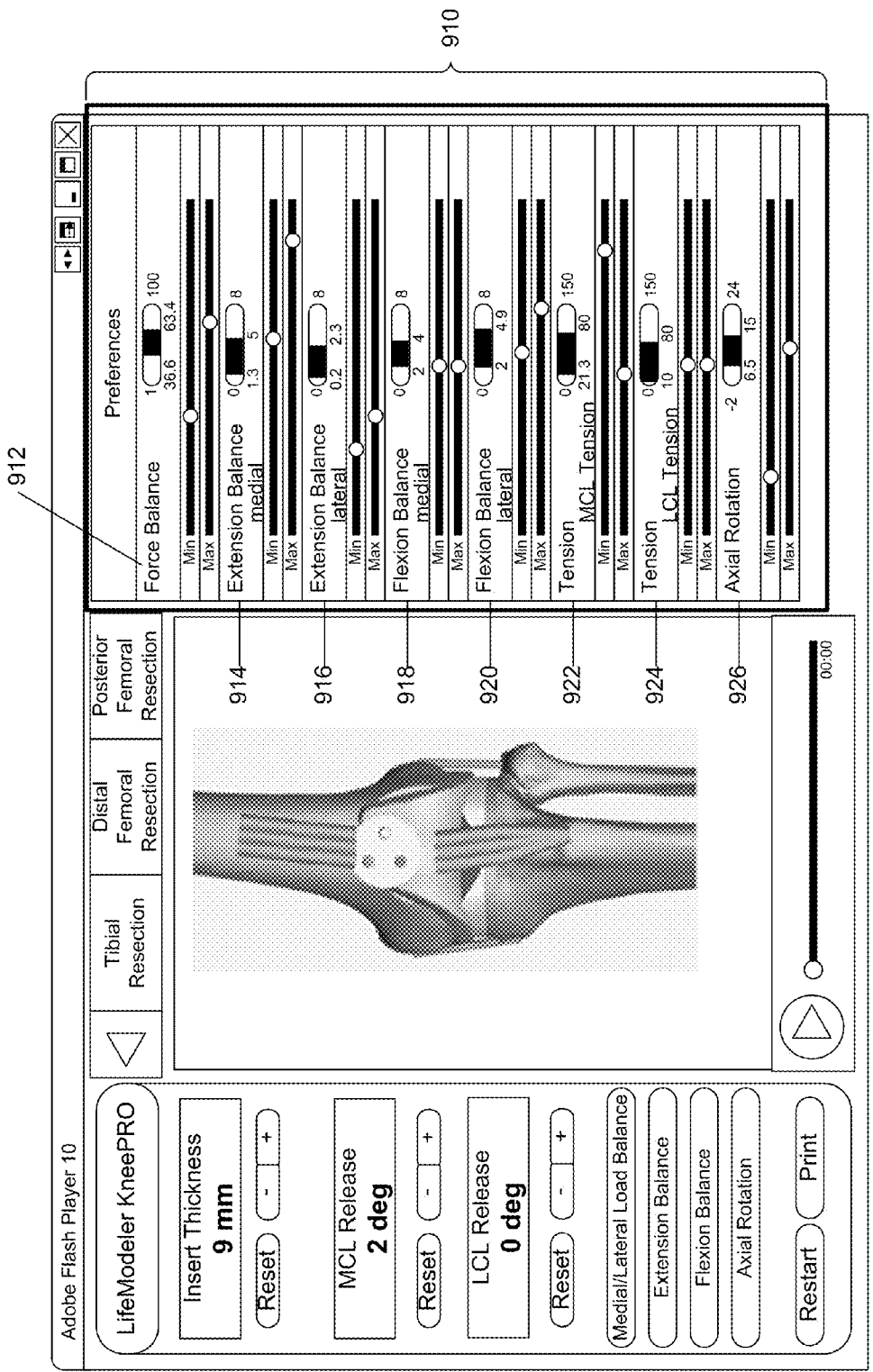
FIG. 9 is an exemplary screen shot of a display of a viewer system in accordance with an embodiment of the invention.

As shown in FIG. 8, the user may next select the trialing tab 810 of the viewer system (displayed on screen 800). The trialing tab 810 replicates the part of the knee replacement operation known as trialing. In this step, the surgeon places in the joint provisional implants, or "trials", which match the geometry of the implants, and are used to test the fit of different components prior to installing the final implant components. The surgeon may put the joint through a series of physical activities (e.g., exercises), and evaluate the soft tissue tensions, joint alignment, and range of motion before making final adjustments to the system.

As on the other tabs, the trialing tab 810 includes multiple control buttons 860, 870, 880 corresponding to surgical factors that are typically adjusted during this step of the procedure. For example, the user may specify the tibial implant thickness using control buttons 860, may adjust the MCL release using control buttons 870, and may adjust the LCL release using control buttons 880. These controls can be manipulated to change the output values.

In the joint modeling application, several different tests 820 are shown, each of which can be animated in the main window, and each of which includes one or more outcome prediction measurements 840. For example, tests 820 may include the following, each represented by a selection button: medial/lateral load balance 822, extension balance 824, flexion balance 826 and axial rotation 828. The outcome prediction measurements or values 840 may include the following: contact (% M/L) 842 and ligaments (lb) 844 (which shows the MCL tension 844*a* and LCL tension 844*b*).

The outcome prediction values 840 are calculated (or retrieved from a database) based on the patient parameters and the surgical parameters entered in the application. Each indicator shows the current value as a vertical line along a scale with green and red ranges. Values in the green range indicate a positive result, and values in the red range suggest that a change to the surgical parameters may be advisable.

Clicking on the preferences panel 850 at the bottom of screen 800 displays control sliders 910 (shown on screen 900 of FIG. 9) allowing the user to adjust the green range for each indicator according to personal preference or experience.

Exemplary sliders 910 include force balance 912, extension balance medial 914, extension balance lateral 916, flexion balance medial 918, flexion balance lateral 920, tension MCL tension 922, tension LCL tension 924, and axial rotation 926.

Figure 10:
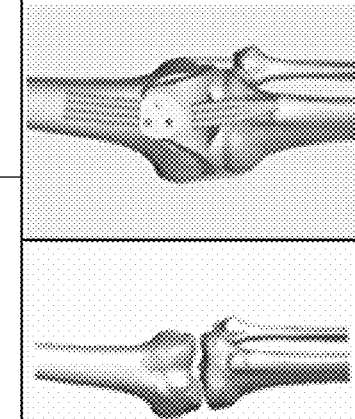
FIG. 10 is an exemplary screen shot of a display of a viewer system in accordance with an embodiment of the invention.

Turning now to FIG. 10, a summary tab 1010 of viewer system is shown (displayed on screen 1000). The summary tab 1010 displays the patient parameters 1020, surgical parameters 1030, and final outputs from the outcome predictions 1040. Tab 1010 may also display "before" 1050 and "after" 1060 images of the knee.

As described herein, the joint modeling application is an example for one joint. However, it should be appreciated that the modeling application may be used for any surgery related to biomechanics (e.g., spine, joints, etc). The same process can be used to build similar tools for other joints by changing the steps as appropriate to replicate the surgical procedure and options for each case.

For example, an application for the hip might have steps of femoral head resection, femoral broaching, acetebular reaming, component sizing/positioning, and trialing. Steps for a spinal fusion case might include placement of pedicle screws, selection of rod materials and diameter, and some functional tests.

The underlying concept is to identify the common, important, or otherwise interesting, factors influencing the outcome of a surgical intervention. Then, by varying these factors, generate a database of possible outcomes. The interface for each application would allow the input factors to be set, so that the correct result could be identified from the database.

Figure 11A:
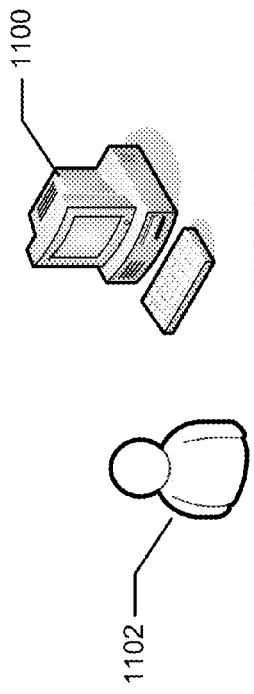
FIG. 11A is a block representation of a computer system and a user in accordance with an embodiment of the invention.

FIG. 11A illustrates a representation of a computer system 1100 and a user 1102. The user 1102 uses the computer system 1100 to perform simulated placement of surgical implants in a patient. The computer system 1100 stores and executes an implant simulation application 1190.

Figure 11B:
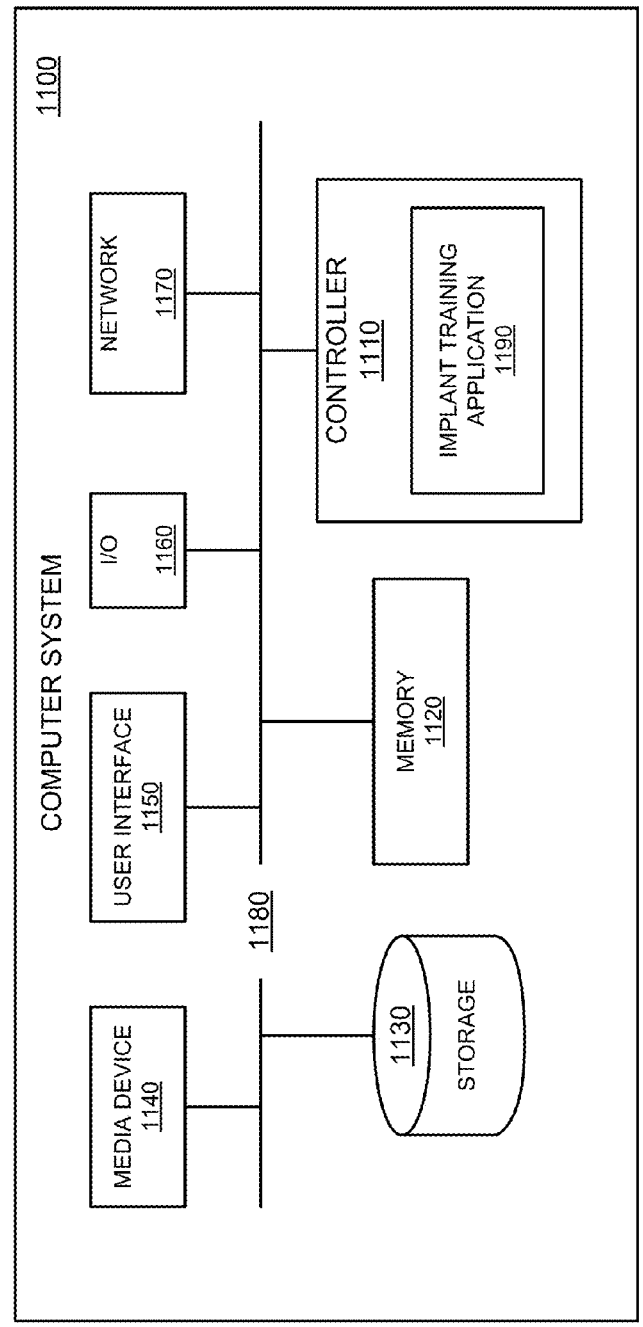
FIG. 11B is a functional block diagram illustrating the computer system of FIG. 11A.

FIG. 11B is a functional block diagram illustrating the computer system 1100 hosting the implant simulation application 1190. The controller 1110 is a programmable processor and controls the operation of the computer system 1100 and its components. The controller 1110 loads instructions (e.g., in the form of a computer program) from the memory 1120 or an embedded controller memory (not shown) and executes these instructions to control the system. In its execution, the controller 1110 provides the implant simulation application 1190 as a software system. Alternatively, this service can be implemented as separate hardware components in the controller 1110 or the computer system 1100.

Memory 1120 stores data temporarily for use by the other components of the computer system 1100. In one implementation, memory 1120 is implemented as RAM. In one implementation, memory 1120 also includes long-term or permanent memory, such as flash memory and/or ROM.

Storage 1130 stores data temporarily or long term for use by other components of the computer system 1100, such as for storing data used by the implant simulation application 1190. Such stored data may include patient parameters, surgical parameters, etc. In one implementation, storage 1130 is a hard disk drive.

The media device 1140 receives removable media and reads and/or writes data to the inserted media. In one implementation, for example, the media device 1140 is an optical disc drive.

The user interface 1150 includes components for accepting user input from the user of the computer system 1100 and presenting information to the user. In one implementation, the user interface 1150 includes a keyboard, a mouse, audio speakers, and a display. The controller 1110 uses input from the user to adjust the operation of the computer system 1700.

The I/O interface 1160 includes one or more I/O ports to connect to corresponding I/O devices, such as external storage or supplemental devices (e.g., a printer or a PDA). In one implementation, the ports of the I/O interface 1160 include ports such as: USB ports, PCMCIA ports, serial ports, and/or parallel ports. In another implementation, the I/O interface 1760 includes a wireless interface for communication with external devices wirelessly.

The network interface 1170 includes a wired and/or wireless network connection, such as an RJ-45 or "Wi-Fi" interface (including, but not limited to 802.11) supporting an Ethernet connection.

The computer system 1100 includes additional hardware and software typical of computer systems (e.g., power, cooling, operating system), though these components are not specifically shown in FIG. 11B for simplicity. In other implementations, different configurations of the computer system can be used (e.g., different bus or storage configurations or a multi-processor configuration).

Various illustrative implementations of the present invention have been described. However, one of ordinary skill in the art will see that additional implementations are also possible and within the scope of the present invention. As was noted above, the same principles can be applied to other joint replacement surgeries and the treatments of other types, for example, injuries to muscles, tendons, and ligaments.

Accordingly, the present invention is not limited to only those implementations described above. Those of skill in the art will appreciate that the various illustrative modules and method steps described in connection with the above described figures and the implementations disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

The various illustrative modules and method steps described in connection with the implementations disclosed herein can be implemented or performed with a general purpose processor, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A general-purpose processor can be a microprocessor, but in the alternative, the processor can be any processor, controller, or microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the implementations disclosed herein can be embodied directly in hardware, in a software module executed by a processor, or in a combination of the two. A software module can reside in computer or machine readable storage media such as RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

The above description of the disclosed implementations is provided to enable any person skilled in the art to make or use the invention. Various modifications to these implementations will be readily apparent to those skilled in the art, and the generic principles described herein can be applied to other implementations without departing from the spirit or scope of the invention. Thus, it is to be understood that the description and drawings presented herein represent example implementations of the invention and are therefore representative of the subject matter which is broadly contemplated by the present invention. It is further understood that the scope of the present invention fully encompasses other implementations.

The invention claimed is:

1. An implant training system comprising:
a processor configured to load and execute instructions from an implant simulation module, said implant simulation module configured to:
provide a preloaded case representing a model patient to a user;
receive input from the user to adjust the preloaded case to represent a particular patient, the input comprising details about a specific surgical approach for the particular patient and including identifying a resection location and a resection angle;
receive resection location and resection angle input from the user to make adjustments to the resection location and the resection angle, the resection location and resection angle input indicating an adjusted resection location and an adjusted resection angle; and
provide outcome information for using an implant in the particular patient at the adjusted resection location and the adjusted resection angle.

2. The system of claim 1, wherein the preloaded case representing a model patient is generated from surgical outcome data derived in part from clinical subject data.

3. The system of claim 1, wherein the preloaded case representing a model patient is generated from surgical outcome data derived in part from simulated subject data.

4. The system of claim 1, wherein information received from the user for a particular patient includes patient data factors that can be measured on the patient prior to surgery.

5. The system of claim 1, wherein the implant simulation module is further configured to: receive input from the user to adjust the implant in the patient.

6. The system of claim 5, wherein the input from the user to adjust the implant includes aligning the implant to cover resected body tissue.

7. The system of claim 1, wherein the outcome information is presented as quantitative data.

8. The system of claim 1, wherein the outcome information is presented as a visual image.

9. The system of claim 1, wherein the implant simulation module is configured to:
receive, from the user, input that specifies one or more physical activities to simulate;
simulate the one or more physical activities; and
provide, based on simulation of the one or more physical activities, data indicating predicted characteristics of ligaments surrounding the implant when the one or more physical activities are performed with the implant at the adjusted resection location and the adjusted resection angle.

10. The system of claim 1, wherein the outcome information includes outcome prediction values indicative of whether surgical parameters should be adjusted.

11. The system of claim 1, wherein the outcome information includes providing a simulation of clinical tests a user may perform.

12. The system of claim 1, wherein the implant simulation module is configured to perform an analysis for each of multiple parameters of the implant at the adjusted resection location and the adjusted resection angle;
wherein providing outcome information comprises providing outcome information in a good/bad format for the analysis of each of the multiple parameters.

13. The system of claim 1, wherein the outcome information is a visual indicator that indicates whether an outcome prediction value for an outcome characteristic fell within or outside a predefined range of acceptable values for the outcome characteristic.

14. The system of claim 13, wherein the visual indicator is a red color for calculated output values that fall outside the predefined range of acceptable values and the visual indicator is a green color for calculated output values that fall within the predefined range of acceptable values.

15. The system of claim 9, wherein the implant simulation module is configured to provide an animation of the implant at the adjusted resection location and the adjusted resection angle moving through the one or more physical activities.

16. The system of claim 9, wherein to provide data indicating predicted characteristics of ligaments surrounding the implant, the implant simulation module is configured to provide data indicating a predicted medial/lateral contact percentage.

17. The system of claim 9, wherein to provide data indicating predicted characteristics of ligaments surrounding the implant, the implant simulation module is configured to provide data indicating a predicted medial/lateral contact percentage a predicted collateral ligament tension.

18. The system of claim 1, wherein the implant simulation module is configured to receive user input that indicates a user-specified range of acceptability for each of multiple joint characteristics; and
wherein to provide outcome information, the implant simulation module is configured to indicate whether predicted joint characteristics are within the user-specified ranges of acceptability.

19. The system of claim 1, wherein the implant simulation module is configured to receive user input that indicates a collateral ligament release; and
wherein to provide outcome information, the implant simulation module is configured to indicate predicted characteristics after performing the collateral ligament release.

20. The system of claim 1, wherein the implant simulation module is configured to:
provide a user interface that allows the user to input user-specified parameters for bone resection, implant positioning, and implant trialing in a simulated joint; and
provide outcome information for the simulated joint according to the user-specified parameters.

21. An implant training system comprising:
a processor configured to load and execute instructions from an implant simulation module, said implant simulation module configured to:
provide, to a user, a preloaded case representing a model patient;
adjust the preloaded case to represent anatomic characteristics of a joint of a particular patient;
receive, from the user, input that indicates a user-specified resection location and a user-specified resection angle;
receive, from the user, input that indicates a user-specified implant characteristic;
receive, from the user, input that indicates a user-specified positioning of an implant with respect to the joint; and
provide outcome information indicating predicted characteristics of the joint having resections at the user-specified resection location and user-specified resection angle and having an implant with the user-specified implant characteristic and user-specified positioning.

22. The system of claim 21, wherein the implant simulation module is configured to receive user input that indicates a user-specified range of acceptability for each of multiple joint characteristics; and
wherein to provide outcome information, the implant simulation module is configured to indicate whether predicted joint characteristics are within the user-specified ranges of acceptability.

23. The system of claim 21, wherein to provide outcome information, the implant simulation module is configured to indicate a predicted extension balance and a predicted flexion balance of the joint.

24. The system of claim 21, wherein to provide outcome information, the implant simulation module is configured to indicate an axial rotation of the joint.

* * * * *